US00PP28700P2

(12) United States Plant Patent
Roberts

(10) Patent No.: US PP28,700 P2
(45) Date of Patent: Nov. 28, 2017

(54) PEPPERMINT PLANT NAMED 'PENDLETON'

(50) Latin Name: *Mentha piperita*
Varietal Denomination: Pendleton

(71) Applicant: Essex Laboratories, Inc., Napavine, WA (US)

(72) Inventor: Donald D. Roberts, Independence, OR (US)

(73) Assignee: ESSEX LABORATORIES, LLC, Chehalis, WA (US)

( * ) Notice: Subject to any disclaimer, the term of this patent is extended or adjusted under 35 U.S.C. 154(b) by 0 days.

(21) Appl. No.: 14/999,510

(22) Filed: May 18, 2016

(51) Int. Cl.
*A01H 5/12* (2006.01)

(52) U.S. Cl.
USPC ..... Plt./259

(58) Field of Classification Search
USPC ..... Plt./259
See application file for complete search history.

(56) References Cited

PUBLICATIONS

Chicago Rabbinical Council Dec. 9, 2015, retrieved on Aug. 22, 2016, retrieved from the Internet at <http://www.crcweb.org/LOC/Lebermuth%20Co%20Inc%20102938.pdf> p. 11.*
Sakurai et al. Pyridine Derivatives in Peppermint Oil, Agric. Biol. Chem., 47 (10), 2307-2312, 1983.*
International Code of Nomenclature for Cultivated Plants Eighth Edition 2009, Scripta Horticulturae No. 10, pp. i-iv, 24-34, 206.*
Fuchs, Sabine, et al., "Biosynthesis of menthofuran in *Mentha×piperita*; Stereoselective and Mechanistic Studies;" J. Agric. Food Chem., 1999, 47(10), pp. 4100-4105.
Hussain, Abdullah I., et al., "Seasonal variation in content, chemical composition and antimicrobial and cytotoxic activities of essential oils from four *Mentha* species," J. Sci. Food Agric., 2010, 90(11), pp. 1827-1836.
Mahmoud, Soheil S., et al., "Menthofuran regulates essential oil biosynthesis in peppermint by controlling a downstream monoterpene reductase," Proc. Natl. Acad. Sci., USA, Nov. 25, 2003; 100(24), pp. 14481-14488.
Rohloff, Jens, et al., "Effect of harvest time and drying method on biomass production, essential oil yield, and quality of peppermint (*Mentha piperita* L.);" J. Agric. Food Chem . 2005, 53(10), pp. 4143-4148.
Rohloff, Jens, "Monoterpene composition of essential oil from peppermint (*Mentha piperita* L.) with regard to leaf position using solid-phase microextraction and gas chromatography/mass spectrometry analysis;" J. Agric. Food Chem., 1999, 47(9), pp. 3782-3786.
Verma, R.S., et al., "Essential oil composition of menthol mint (*Mentha arvensis*) and peppermint (*Mentha piperita*) cultivars at different stages of plant growth from Kumaon Region of Western Himalaya," J. Medicinal and Aromatic Plants, 2010, vol. 1(1), pp. 13-18.

* cited by examiner

*Primary Examiner* — June Hwu
(74) *Attorney, Agent, or Firm* — Marger Johnson

(57) ABSTRACT

Mint selection 13-39-9, denominated 'Pendleton' peppermint is a new *Mentha piperita* cultivar that produces an essential oil different in composition and has a compact plant type and resistance to mint rust (*Puccinia menthae*) and mint wilt (*Verticillium dahliae*).

2 Drawing Sheets

Latin name of the genus and species: *Mentha piperita.*
Variety denomination: 'PENDLETON'.

FEDERAL SPONSORSHIP

None

TYPE OF PLANT AND NAME OF VARIETY

The present invention relates to a new and distinct variety of peppermint plant developed from a parent of the species *Mentha piperita* L. The new mint variety will be identified as 'Pendleton'.

BACKGROUND OF INVENTION

'Pendleton' originated as a seedling from an open pollinated polyploid *M. piperita* seedling parent, identified as 11-14-8. Seedling 11-14-8 was selected in 2011 from a population of fertile *M. piperita* plants. The parent to 'Pendleton' was one of several mint lines in a polycross breeding system composed of selected male and female fertile polyploid genotypes.

DISCOVERY AND ASEXUAL REPRODUCTION

This new mint was developed in a mint breeding program in which the primary objective was to develop a mint variety having a specific oil composition, acceptable yield and resistant to mint diseases. The new variety is more resistant to mint wilt (soil-borne fungus *Verticillium dahliae*) and mint rust (air-borne fungus *Puccinia menthae*) than its parent. Selection 'Pendleton' has an equivalent oil yield to the control variety 'Black Mitcham' in test plots since 2013. This plant was selected from a population of mint seedlings in research plots on land near Monmouth, Oreg., and initially identified as 13-39-9.

'Pendleton' is asexually propagated to maintain the cultivar's genetic integrity and as a means of increasing the selection for commercial planting. Asexual propagation, by tip cuttings or stolon sections, is a common practice in commercial mint cultivation and serves as a means of propagating the normally sterile mint plant. The same propagation techniques of tip cuttings or stolon sections are used with 'Pendleton' as with commercial mint cultivation. 'Pendleton' produces a moderate number of stolons to allow propagation by this means. The inventor has conducted asexual propagation of 'Pendleton' for greenhouse and field planting in Monmouth, Oreg., each year since 2013 and the genotype comes true to form with each generation.

SUMMARY OF THE INVENTION

Mint selection 13-39-9, denominated 'Pendleton' is a new *Mentha* sp. cultivar that produces an essential oil different in composition than commercially grown mint varieties. The essential oil is similar to standard mint oil in components composition but differs in the typical ratio of components. Organoleptically it differs from typical *Mentha piperita* peppermint oil. It is more resistant to mint rust *Puccinia menthae* and more resistant to *Verticillium dahliae* mint wilt than current commercially grown varieties.

BRIEF DESCRIPTION OF THE FIGURES

The accompanying color figures show typical greenhouse and vegetative growth of 'Pendleton' and depicts the color as nearly true as reasonably possible.

FIG. 1 illustrates the flowering pattern and multiple flowering shoots of my new mint plant in accordance with the present invention.

FIG. 2 illustrates the shape of the flower and leaf collected from a one-year-old field grown plant.

DESCRIPTION OF PLANT

My new mint plant improves upon and is distinct from other mint plants in several characteristics, including but not limited to, the following:

1. The ability to produce an essential oil different in composition but with similar components as 'Black Mitcham' peppermint;
2. A more compact plant but with a branching pattern similar to its parent;
3. An early spring growth similar to 'Black Mitcham' peppermint but with an earlier maturity for desirable chemical composition of its essential oil;
4. A level of resistance to mint wilt (*Verticillium dahliae*) equal to or greater than that of its parent;
5. Resistance to mint rust caused by *Puccinia menthae.*

The essential oil extracted from 'Pendleton' has the same components as that of commercial oil produced by 'Black Mitcham' peppermint as illustrated in Table 1. However, the ratio of oil components differs between the commercial peppermint oil and that of 'Pendleton'. The concentration of menthone and menthol in the oil of 'Pendleton' is lower than that of 'Black Mitcham'. The amount of menthofuran in the oil of 'Pendleton' is higher than that of 'Black Mitcham'. Organoleptically, the oil of 'Pendleton' is different from that of 'Black Mitcham', reflecting the difference in oil component ratios.

TABLE 1

Composition of 'Pendleton' Oil from Test Plots Compared to Commercial 'Black Mitcham'v Peppermint Oil and Oil from 'Black Mitcham' Peppermint Grown in Test Plots located near Monmouth, Oregon.

| Essential Oil Components | Commercial 'Black Mitcham' 1/ | 2005 Test Plot 'Black Mitcham' 2/ | 2015 Test Plot 'Pendleton' |
|---|---|---|---|
| 1-Limonene | 1.78 | 1.73 | 3.20 |
| 1,8-Cineole | 5.33 | 4.90 | 5.60 |
| 1-Menthone | 20.00 | 19.43 | 15.50 |
| Menthofuran | 4.35 | 4.23 | 28.60 |
| Iso-menthone | 3.19 | 3.14 | 1.50 |
| 1-Menthyl acetate | 5.09 | 5.36 | 4.90 |
| Neo-menthol | 5.40 | 5.52 | 2.10 |
| 13-caryophyllene | 0.83 | 0.85 | 0.60 |
| 1-Menthol | 45.20 | 44.60 | 26.20 |
| Pulegone | 2.17 | 2.14 | 0.80 |
| Germacrene-D | 1.22 | 1.37 | 1.20 |

The numbers listed in the above table are percentages based upon the analysis of the respective mint oils by gas chromatography. The percentages are determined by calculation of the relative peak areas.
1/ Commercial oil sample typical of what is produced by mint growers.
2/ 'Black Mitcham' oil from a control plant in the 2005 test plot.

TAXONOMIC DESCRIPTION OF 'PENDLETON'

This new mint plant, under greenhouse and field growing conditions, is a bush type plant with lateral branches at each node of the main stems. The height of 'Pendleton' is slightly less than 'Black Mitcham' growing under similar conditions and will vary based on fertilizer, soil quality, and water application, amongst other known factors that affect growth patterns. 'Pendleton' is between 0.3 and 0.5 m at mid-stem in width and 0.9 to 1.2 m in height under greenhouse environment. Field grown 'Pendleton' has a width of 0.3 to 0.5 m and a height of 0.8 to 1.2 m. Secondary and tertiary branching occurs to form a compact growth habit. When 'Pendleton' is mature and ready for harvest, the main stem at mid-plant (approximately between the eleventh and twelfth node) is 4.9-5.4 mm in width. The secondary and tertiary branch stems are 2.5-3.0 mm and 1.7-2.0 mm in width, respectively. The stems are square, glabrous, and a green color that matches The Fifth Edition Royal Horticultural Society Colour Chart 143B green group, with a strong anthocyanin intensity.

Mature leaves at the bottom of the plant are ovate to elliptical as are leaves on secondary branch stems. Leaves on upper mature plants, both main and secondary stems, are more elliptical with an obtuse tip and oblique base (FIG. 2). The adaxial leaf surface is glabrous. The abaxial leaf surface is sub-glabrous with oil glands distributed across the surface. Mid-main stem leaf size at flowering is 28-32 mm in width and 56-60 mm in length. Leaf size on secondary branches at flowering is 18-20 mm in width and 30-35 mm in length. Leaf petioles are sub-glabrous on the main stem leaves and petioles are light green in color that matches The Fifth Edition Royal Horticultural Society Colour Chart 138B green group, and are 11-12.5 mm in length while petioles on secondary branch stem leaves are 6-7 mm in length. Leaves on the mid-main stem and lower tend to be slightly lobed and denticulate while the leaves on the upper plant tend to be more dentate. The main stem leaves are toothed having from 20-22 teeth on each side. Secondary branch leaves have 12-13 teeth on each side. The adaxial leaf is dark green in color, ranging from The Fifth Edition Royal Horticultural Society Colour Chart 137B to 137C in the green group classification. The color of the abaxial leaf surface is a green color that matches The Fifth Edition Royal Horticultural Society Colour Chart 144A, yellow-green group. The leaf has 6-9 lateral veins, more or less in parallel off the main vein that runs from the petiole to the tip of the leaf. The veins are prominent in all leaves of 'Pendleton'.

The inflorescence is a cyme with capitate flowers developing at the nodes and tip of the stern. The average number of flowers per inflorescence of 'Pendleton' did not vary significantly from the average number for mint plants in the closest varieties of *Mentha piperita* and 'Black Mitcham', which have 2-20 flowers per inflorescence. The average length of the peduncle of 'Pendleton' did not vary significantly from the average length for mint plants in the closest varieties of *Mentha piperita* and 'Black Mitcham', in which the peduncle ranges from 0 mm (sessile) to 20 mm for mature blooms. Similarly, the surface texture of the peduncle of 'Pendleton' did not vary significantly from the surface texture for mint plants in the closest varieties of *Mentha piperita* and 'Black Mitcham', in which the peduncle is scabrid. Finally, the color of the peduncle of 'Pendleton' did not vary significantly from the peduncle colors for mint plants in the closest varieties of *Mentha piperita* and 'Black Mitcham', which range from the light yellow green group (147C) to the greyed purple group (187A) as illustrated in The Fifth Edition Royal Horticultural Society Colour Chart. The capitate flowers are 20-22.5 mm in width and 17.5-20 mm in length. The flowers consist of five petals fused into a two lipped corolla. Both the inner and outer surfaces of the corolla is light violet in color ranging from The Fifth Edition Royal Horticultural Society Colour Chart 85C-85D in the violet group. The average size of the calyx of 'Pendleton' did not vary significantly from the average for mint plants in the closest varieties of *Mentha piperita* and 'Black Mitcham', in which the calyx ranges from 1-5 mm in length and is about 1 mm in diameter. Both the inner and outer surface of the calyx is generally yellow-green and is 143C-143D of The Fifth Edition Royal Horticultural Society Colour Chart, green group. Additionally, the surface texture of the calyx of 'Pendleton' did not vary significantly from the surface texture for mint plants in the closest varieties of *Mentha piperita* and 'Black Mitcham', in which the calyx is smooth or glabrous at the base, but then hairy or rough at the teeth. The gynoecium consists of a single pistil with two lobed stigma that is exserted. The androecium consists of four stamens, each with a distinct filament and anther. The bloom season for 'Pendleton' under field conditions is in July and August.

Seed produced by 'Pendleton' varies in color from brown in The Fifth Edition Royal Horticultural Society Colour Chart 177A, greyed-orange group, to black in The Fifth Edition Royal Horticultural Society Colour Chart 203B, black group. The seeds are oval in shape with a width of 0.4 to 0.6 mm and a length of 0.6 to 0.8 mm.

While the plant that comprises the present invention has been described in connection with a specific embodiment thereof, it will be understood that this application is intended to cover any variation, uses, or adaptation of the invention (particular those induced by cultivation under different environmental conditions) following, in general, the principles of the invention and including such departures from the present disclosures as come within known or customary practice in the art to which the invention pertains and as may be applied to the essential features hereinbefore set forth, and as fall within the scope of the invention and the limits of the appended claim.

I claim:

1. A new and distinct variety of peppermint plant, substantially as shown and described, characterized particularly by improving resistance to mint rust and mint wilt, and producing a unique essential oil.

* * * * *

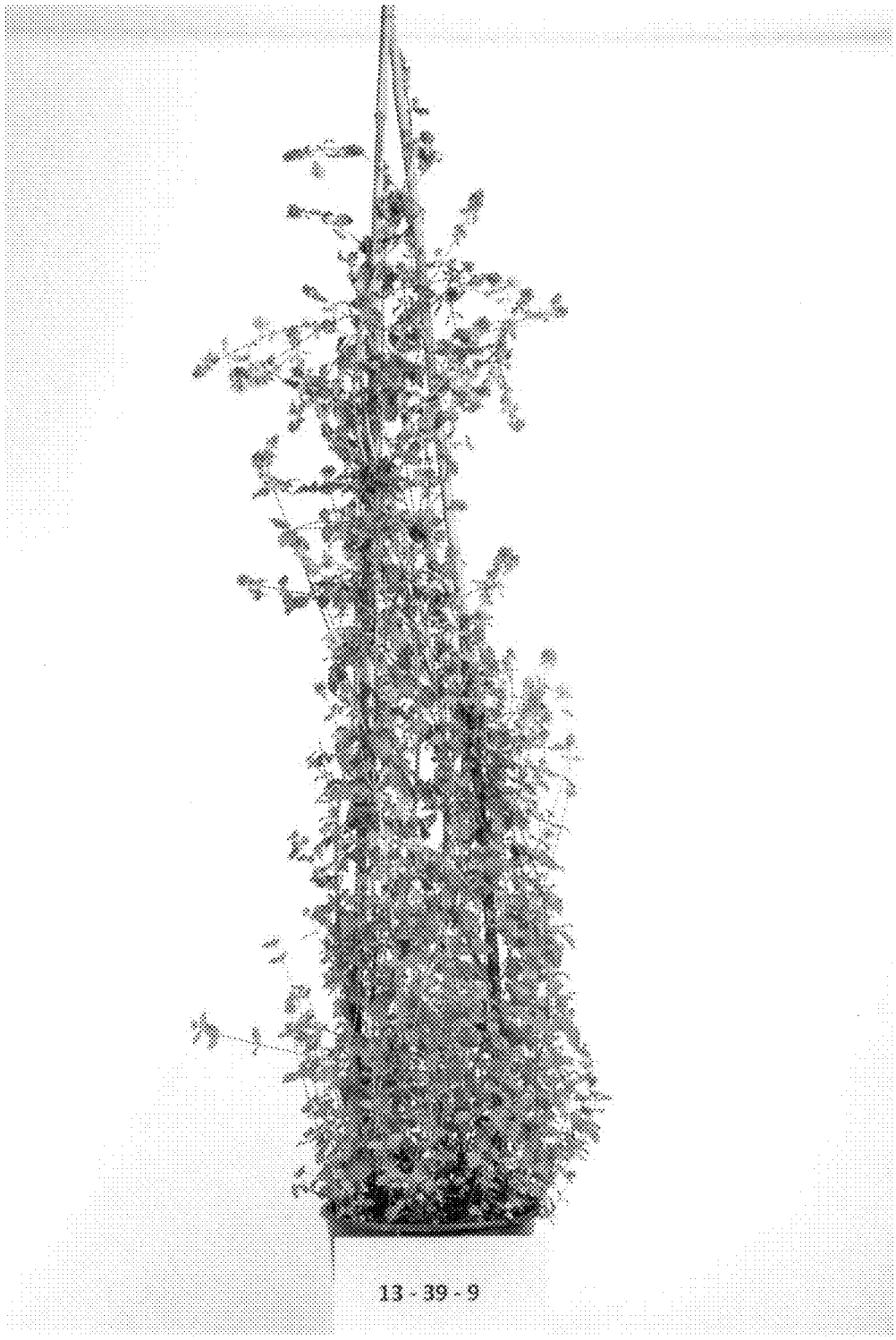
13 - 39 - 9

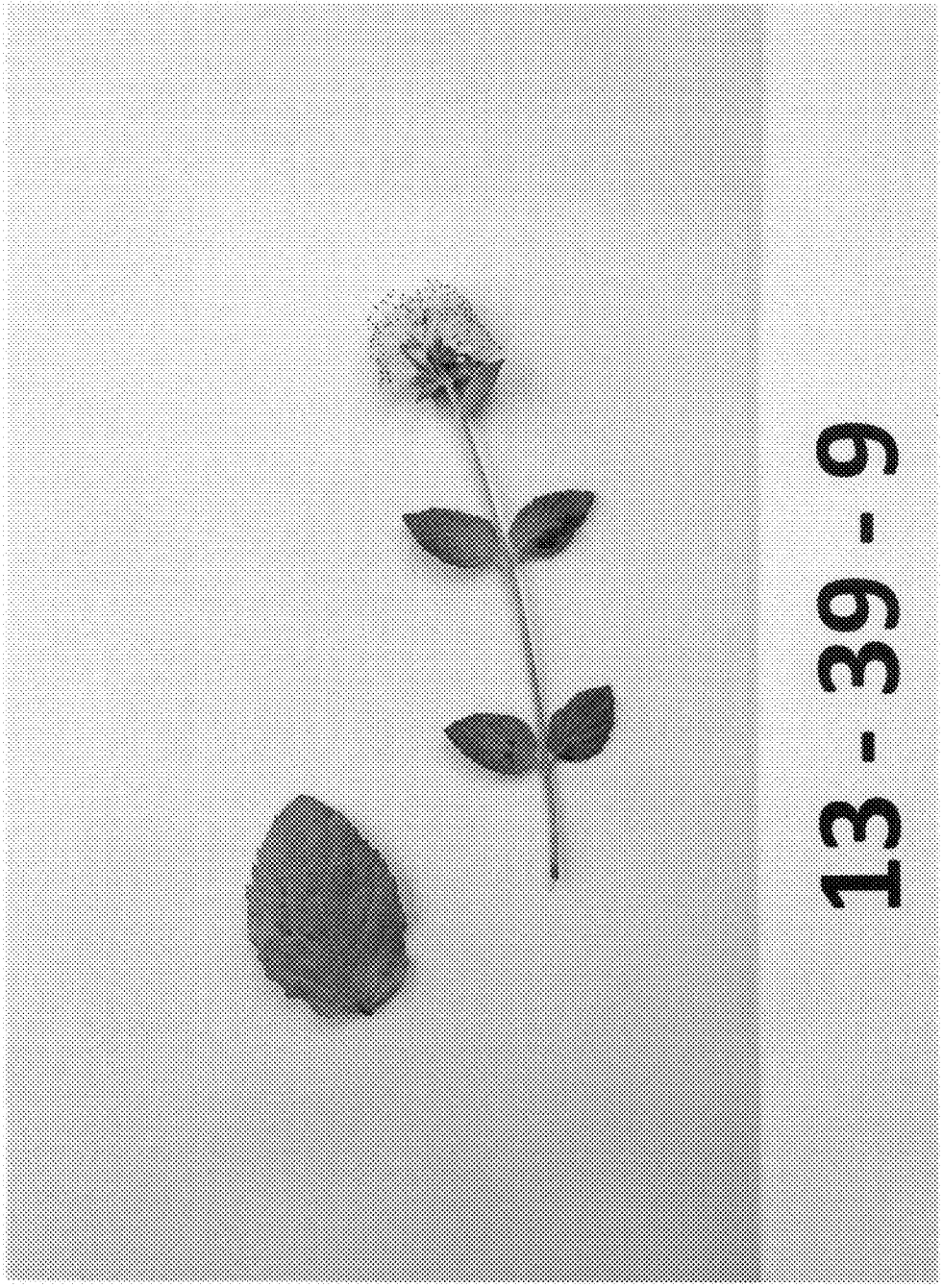
13-39-9